United States Patent [19]

Fändriks et al.

[11] Patent Number: 5,977,159
[45] Date of Patent: Nov. 2, 1999

[54] MEDICAL USE OF AN ACE-INHIBITOR FOR TREATMENT OF DYSPEPTIC SYMPTOMS

[75] Inventors: Lars Fändriks, Askim; Anders Pettersson, Kode, both of Sweden

[73] Assignee: Astra Aktiebolag, Sodertalje, Sweden

[21] Appl. No.: 08/793,059

[22] PCT Filed: Dec. 20, 1996

[86] PCT No.: PCT/SE96/01733

§ 371 Date: Feb. 13, 1997

§ 102(e) Date: Feb. 13, 1997

[87] PCT Pub. No.: WO97/26014

PCT Pub. Date: Jul. 24, 1997

[30] Foreign Application Priority Data

Jan. 15, 1996 [SE] Sweden .................................. 9600120

[51] Int. Cl.[6] .................................................. A61K 31/40
[52] U.S. Cl. ............................................................ 514/423
[58] Field of Search ............................................... 514/423

[56] References Cited

U.S. PATENT DOCUMENTS 5,686,451 11/1997 Kristianson et al. ................ 514/223.5

OTHER PUBLICATIONS

Indian J. Physiol Pharmacol., vol. 39, No. 3, 1995, pp. 296–298, Rao, et al., Effect of Angiotensin Converting Enzyme Inhibitor (Captopril) on Gastric Ulcer Production in Pylorus Ligated Rats.

Indian J. Physiol Pharmacol., vol. 34, No. 3, 1990, pp. 206–208, D'Souza et al., Comparison of the Effects of Captopril and Enalapril on Oxyphenbutazone and Ethanol–Induced Gastric Lesions in Rats.

*Primary Examiner*—Raymond Henley, III
*Attorney, Agent, or Firm*—White & Case L.L.P.

[57] ABSTRACT

A method for the prophylaxis and treatment of dyspeptic symptoms of unknown origin using ACE-inhibitors and a pharmaceutical peparation comprising these compounds.

5 Claims, No Drawings

MEDICAL USE OF AN ACE-INHIBITOR FOR TREATMENT OF DYSPEPTIC SYMPTOMS

This application is a 371 of PCT/SE96/01733 filed Dec. 20, 1996.

FIELD OF INVENTION

The present invention is related to the use of ACE-inhibitors for the prophylaxis and/or treatment of dyspeptic symptoms of unknown origin and to the manufacture of medicaments with effect on such dyspeptic symptoms.

BACKGROUND OF THE INVENTION

Functional disorders of the gastrointestinal tract are common and account for a very large number of medical consultations. On an annual basis approximately 30% of the western population experience such functional dyspeptic symptoms varying from mild indigestion to severe pain. The symptomatology may be due to an organic disease (for example peptic ulcer disease) or, more commonly, be without any known origin (i.e. absence of organic pathology in the upper gut as evidenced by various diagnostic procedures). In clinical routine the latter symptom-syndrome is commonly called "non-ulcer dyspepsia", "functional dyspepsia", or "non-organic dyspepsia". Current treatment of dyspepsia with unknown origin involves a variety of pharmacological principles, e.g. neutralization of gastric acidity or affecting the motility of the gut wall, some of which have doubtful efficacy and sometimes have severe side effects.

Dyspepsia due to peptic ulcer can be cured by intake of antacids and inhibitors of gastric acid secretion. Ulcer-like dyspeptic symptoms, also without mucosal pathology, usually respond to similar treatment. This sub-population of dyspeptic symptoms (acid-related dyspepsia) is thus defined by the symptom-relief in association with intake of neutralizing agents or of inhibition of gastric acid production by use of proton pump inhibitors or histamine H2-receptor antagonists. However, the former treatment is short-lasting and neutralizing drugs must be administered repeatedly during the day. The latter treatment has disadvantages of being expensive and exerting an impact on the gut physiology, as the antacid gastric conditions increase the risk for intestinal and/or systemic infections. Prokinetic drugs (such as cisapride) or anticholinergic compounds are other agents that are utilized to cure dyspeptic symptoms, usually with variable efficiency and high frequency of side effects. It follows that available drug regimens for treating dyspeptic symptoms are impaired by certain disadvantages.

The present invention relates to a new method of treating dyspepsia with unknown origin by pharmacological interference with the renin-angiotensin system (RAS).

PRIOR ART

Compounds that interfere with the renin-angiotensin system (RAS) are well known in the art and are used to treat cardiovascular diseases, particularly arterial hypertension and cardiac failure. Principally, the RAS can be interferred with by inhibition of the enzymes synthesizing angiotensins or by blocking the corresponding receptors at the effector sites. Available today are renin antagonists, inhibitors of the angiotensin converting enzyme (ACE) and angiotensin II-receptor (AII-receptor) antagonists. In addition to cardiovascular effects, some of these compounds have been claimed to exert effects on unspecified "gastrointestinal disorders".

DETAILED DESCRIPTION OF THE INVENTION

It has surprisingly been found that antihypertensive treatment by use of an angiotensin converting enzyme (ACE) inhibitor decreases the frequency and severity of dyspeptic symptoms of unknown origin (such as "non-ulcer dyspepsia," functional dyspepsia or "non-organic dyspepsia") and can act in a prophylactive manner against these symptoms. The invention describes a new method to treat dyspeptic symptoms of unknown origin by administration of an ACE-inhibitor which interferes with the synthesis of angiotensin II.

The ACE-inhibitor can be administered orally, rectally or parenterally, in neutral form or in the form of a salt. While the effects on dyspeptic symptoms have been established by the peroral route, it is considered that the effect of ACE-inhibitors is a systemic effect, which is not dependent on mode of administration.

The dose of ACE-inhibitors to be administered for the treatment of dyspeptic symptoms will vary depending on factors such as the severity of the disease and the status of the patient. The dosage range at oral, rectal as well as intravenous administration will preferably be in the range from 0.01 to 50 mg per day.

Examples of ACE-inhibitors which can be used for the prophylaxis and for treatment of dyspeptic symptoms are the following:

alacepril
alatriopril
altiopril calcium
ancovenin
benazepril
benazepril hydrochloride
benazeprilat
benzazepril
benzoylcaptopril
captopril
captopril-cysteine
captopril-glutathione
ceranapril
ceranopril
ceronapril
cilazapril
cilazaprilat
converstatin
delapril
delapril-diacid
enalapril
enalaprilat
enalkiren
enapril
epicaptopril
foroxymithine
fosfenopril
fosenopril
fosenopril sodium
fosinopril
fosinopril sodium
fosinoprilat
fosinoprilic acid
glycopril
hemorphin-4
idrapril
imidapril
indolapril indolaprilat
libenzapril
lisinopril
lyciurmin A
lyciumin B
mixanpril
moexipril
moexiprilat
moveltipril
muracein A
muracein B
muracein C
pentopril
perindopril
perindoprilat
pivalopril
pivopril
quinapril
quinapril hydrochloride
quinaprilat
ramipril
ramiprilat
spirapril
spirapril hydrochloride
spiraprilat
spiropril
spiropril hydrochloride
temocapril
temocapril hydrochloride
teprotide
trandolapril
trandolaprilat
utibapril
zabicipril
zabiciprilat
zofenopril
zofenoprilat Where applicable, a compound listed above may be used in racemic form or in the form of a pure or substantitally pure enantiomer.

PHARMACEUTICAL FORMULATIONS

Conventional pharmaceutical preparations can be used. The pharmaceutical preparations may be in the form of injection solutions, oral solutions, rectal solutions, suspensions, tablets for oral or sublingual use or capsules.

The pharmaceutical preparation contains between 0.001 mg and 100 mg of active substance, preferably 0.1 to 50 mg.

CASE REPORT

Case. Male, 37 years old, self employed in yacht construction, has for long time suffered from abdominal discomfort, especially during years of economical recession. The patient was subjected to a single-blind test. During one fortnight he consumed placebo and during another fortnight he received the ACE-inhibitor enalapril (2.5 mg once daily). During enalapril-treatment the subject noted clear symptom-relief and decreased his consumption of antacids compared to the placebo-period.

We claim:

1. A method for the prophylaxis and/or treatment of dyspeptic symptoms of unknown origin in mammals, which comprises administering an effective amount of an ACE-inhibitor or a physiologically acceptable salt thereof to a mammalian host in need of such prophylaxis and/or treatment.

2. The method according to claim 1, wherein the ACE-inhibitor is selected from the group consisting of alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat.

3. The method according to claim 1 or 2, which comprises administering the ACE-inhibitor or salt thereof in association with a pharmaceutically acceptable carrier.

4. The method according to claim 1 or 2, wherein the ACE-inhibitor or salt thereof is administered orally, rectally or intravenously.

5. The method according to claim 4, wherein the dosage range of the administered compound is from 0.01 to 50 mg per day.

\* \* \* \* \*